United States Patent [19]

Köster et al.

[11] Patent Number: 5,142,504
[45] Date of Patent: Aug. 25, 1992

[54] ULTRA-SOUND DETECTOR

[75] Inventors: Harry Köster, Hamburg; Norbert Hoogen, Glinde; Klaus Blickle, Geesthacht, all of Fed. Rep. of Germany

[73] Assignee: Blohm + Voss International GmbH, Hamburg, Fed. Rep. of Germany

[21] Appl. No.: 685,402

[22] Filed: Apr. 12, 1991

[30] Foreign Application Priority Data

Apr. 12, 1990 [DE] Fed. Rep. of Germany ....... 4011923

[51] Int. Cl.[5] .............................................. G01S 15/00
[52] U.S. Cl. ...................................... 367/99; 367/908; 73/290 V
[58] Field of Search .................... 367/908, 902, 99; 73/290 V; 340/621

[56] References Cited

U.S. PATENT DOCUMENTS 4,868,797 9/1989 Soltz ................................... 367/908

*Primary Examiner*—Daniel T. Pihulic
*Attorney, Agent, or Firm*—Nils H. Ljungman & Associates

[57] ABSTRACT

A process for detecting a phase boundary surface between layers of fluids which are not intermixable with one another includes the steps of penetrating at least one of the fluids with sound waves to strike a reflector, receiving the reflected sound waves, comparing the transmitted sound waves to the reflected and received sound waves, using the comparison to determine the acoustic propagation impedance, and using the results to determine the position of the phase boundary layer.

19 Claims, 1 Drawing Sheet

ULTRA-SOUND DETECTOR

BACKGROUND OF THE INVENTION

1. Field of the Invention

The present invention relates to a process for the detection of phase boundary surfaces between layers of different fluids which are not intermixable with one another, and which can be separated from one another by gravity separation, and to a measurement apparatus for the performance of the process.

2. Background Information

Various processes exist for the detection of phase boundary surfaces between layers of dissimilar fluids which are not mixable and which can be separated by gravity separation. The pressure level and the specific gravity of the different fluids can be measured, and the phase boundary surface can be calculated by determining the ratio of the specific gravities and normalizing the result to the measured pressure level. Such processes may prove unsatisfactorily if, for example, the specific gravity of one of more of the participating fluids fluctuates significantly, if the specific gravity cannot be determined with sufficient accuracy, or if the measurements can be distorted by the type of process control in the container containing the liquids, which can occur, for example, as a result of the superimposition of external pressure fluctuations on account of acceleration processes within the fluids, or as a result of other external hydrostatic influences.

There also exist conductive measurement methods, in which the electrical conductivity of the fluids is measured, if there is a significant difference between the electrical conductivity of the different fluids. These methods have the disadvantage that at least one of the fluids covers the sensor electrodes on account of its adhesion and viscosity, and there is no automatic, process-controlled cleaning, so that the measurement values may be distorted.

There also exist capacitive measurement methods, in which the dielectric constant is measured in the presence of at least one electrically non-conducting fluid. This measurement process fails if the conductivity of the non-conducting phase exceeds the value of 10 to 50 milli- Siemens, for example. Such a situation can occur if two fluids which normally cannot be mixed with one another form an intermediate phase in the form of a stable emulsion. Such an emulsion can occur, for example, in a multi-phase system such as water (e.g., seawater) and organic fluids. In the presence of a natural or synthetic emulsifying agent, a stable emulsion can be formed. The boundary layer between such an emulsion with, for example, a seawater proportion of more than 50%, which floats on account of its lower specific gravity, and the free water in the sump of a container or apparatus cannot be detected by capacitive measurement, on account of the fact that the conductivity of the emulsion is similar to that of the water.

It is also possible to monitor the movement of a phase boundary surface by measuring the specific gravity. A prerequisite for such monitoring is that there must be significant differences between the specific gravity parameters. This process cannot be used if viscosities which are significantly different from that of water, for example, up to several thousand centi-Stokes, must be processed, since the reaction of the measurement apparatus over time is very strongly influenced by the self-cleaning characteristics of the sensor, which has a conventional tubular shape and carries the flow.

Other viscosity measurement processes which exist require that there must be significant differences in the viscosities of the different fluids. In many cases, however, the viscosity values of different fluids which cannot be mixed and can be separated by gravity separation are very similar, such as for water and light oils or petroleum from certain producing regions, for example.

To detect phase boundary surfaces, there also exist sonar processes, by means of which the speed of sound in fluids is measured perpendicular to the phase boundary surface. For example, sound waves are transmitted, preferably from below, by a transmitter toward the phase boundary surface. The sound waves are reflected by the phase boundary surface. The propagation time or "echo time" of the sound waves is then evaluated as a yardstick for the distance of the phase boundary surface. The receiver for the reflected sonar signals can be located in the immediate vicinity of the sensor. It is also possible to configure the sensor and receiver as acoustic transformers. Since the sonar process is based physically on a distance measurement, it cannot be used (e.g., will not necessarily yield accurate results) if a significant proportion of the sound waves are reflected diffusely on the phase boundary surface. Such a diffuse reflection occurs if a fluid phase represents an emulsion having a viscosity which is significantly higher than the other fluid, or if the phase boundary surface permanently changes its structure and position on account of flow (e.g., current) factors or movements of the container, which occurs, for example, in the tank of a ship.

In order to overcome the above-noted disadvantages of the measurement processes described above, attempts have been made to use measurement devices with different sensors, by means of which several of the measurement processes described above can be combined. Such multi-sensor arrangements, however, are technically very complex and require a very complex evaluation system. Accordingly, the use of such multi-sensor measurement devices is very expensive.

OBJECTS OF THE INVENTION

One object of the present invention is the provision of a process for the detection of a phase boundary surface or of a layer of a combination of fluids which are not mixable, and a measurement apparatus for the performance of the process which is simple, relatively insensitive to interference, reliable and which makes possible a very precise measurement evaluation.

SUMMARY OF THE INVENTION

According to the invention, these and other objects are achieved by means of a process and by means of a measurement apparatus described herein.

According to one aspect of the invention, only a single sensor is necessary to achieve a clear signal with a high resolution, even for difficult measurements, e.g., measurements of oil-water emulsions and free seawater. This signal indicates clearly whether the phase boundary surface of a combination of non-mixable fluids with different specific gravities, such as aqueous phases and organic fluids, is located above or below a fixed measurement point. The electrical conductivity of one or all phases, the viscosity, changing specific gravities and the formation of emulsified intermediate phases has no effect on the quality of the measurement. The measurement process is not adversely affected by motion. That is, the invention can be advantageously employed, for example, on equipment which is moving in rough seas.

Operation is also possible under the explosion proof (or flame-proof) requirements for so-called "Zone 0" hazardous locations. Preferred areas of application of the inventive process and measurement devices constructed according to the invention are level detectors and phase boundary surface detectors in the entire field of offshore technology, petrochemicals, oil transportation and consumption, and the process technology industry in general.

In summary, one feature of the invention resides broadly in a process for the detection of a boundary surface between a first fluid and a second fluid, the boundary surface being located between a first layer of the first fluid and a second layer of the second fluid, said process comprising the steps of: providing an acoustic source for generating transmitted sound waves when actuated; positioning said acoustic source such that said transmitted sound waves propagate through at least one of the first and second layers of fluids during said actuation of said acoustic source; providing reflector means for being impinged upon by said transmitted sound waves and for reflecting said impinging transmitted sound waves to produce reflected sound waves; said reflector means being positioned a distance from said acoustic source and defining a zone of measurement therebetween; providing receiver means for receiving said reflected sound waves and for registering the reception of said reflected sound waves; actuating said acoustic source to thereby generate said transmitted sound waves; registering the reception of said reflected sound waves with said receiver means; comparing said transmitted sound waves generated by said acoustic source to said reflected sound waves received by said receiver means; employing the results of said comparison to determine at least the acoustic propagation impedance within said zone of measurement; using at least said determined acoustic propagation impedance to determine the position of the boundary layer between the first and second layers of fluids.

BRIEF DESCRIPTION OF THE DRAWING

The invention is explained in greater detail below with reference to the accompanying drawing, which schematically illustrates a measurement apparatus according to one aspect of the invention, and wherein.

DESCRIPTION OF THE PREFERRED EMBODIMENT

Figure 1:
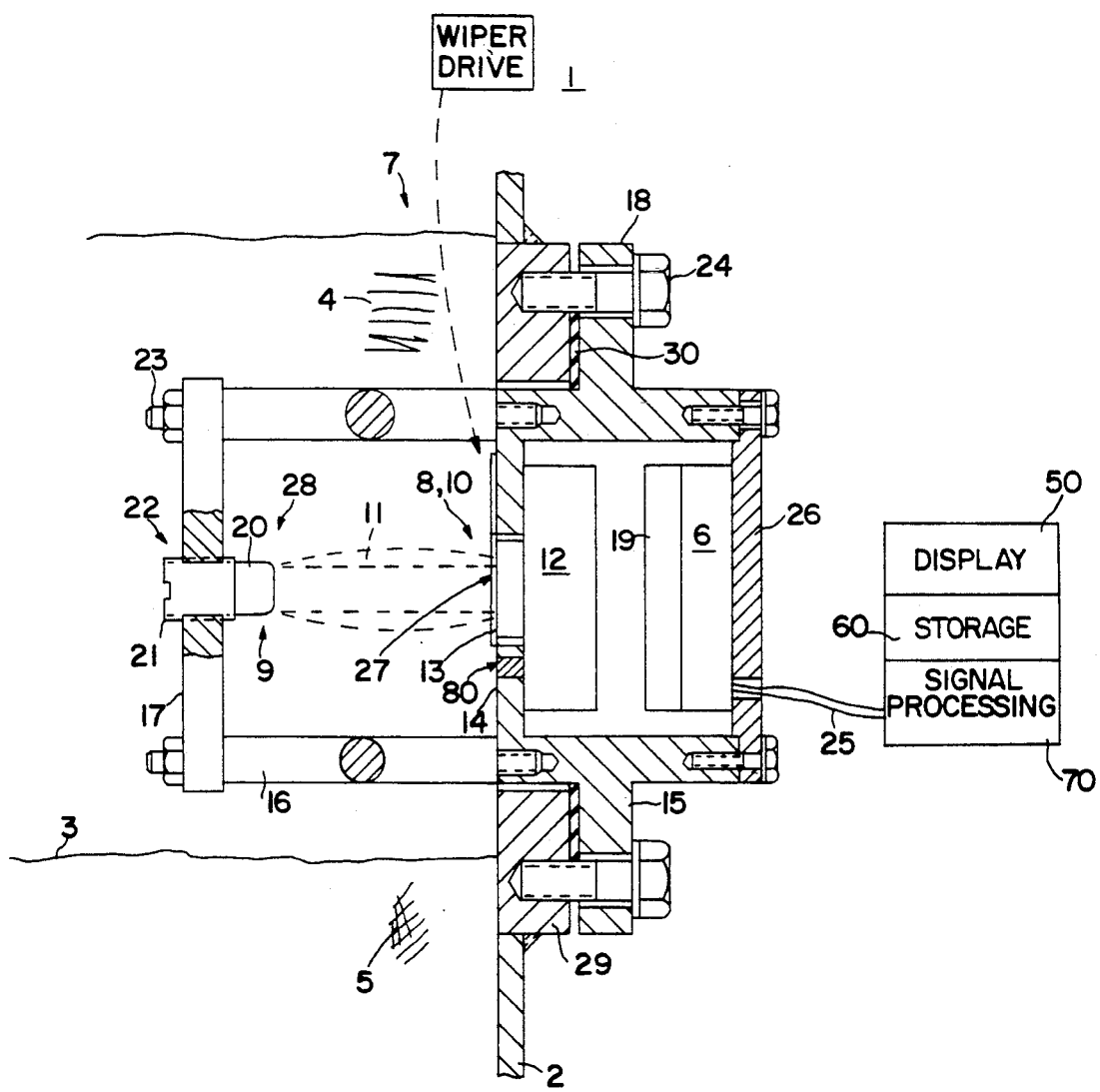
FIG. 1 is an elevational sectional view of a measurement apparatus constructed according to one aspect of the present invention.

A measurement apparatus 1 constructed according to one aspect of the present invention includes a sensor 7 and an electronic evaluation unit 6. The sensor 7 and the evaluation unit 6 are connected to one another. The sensor 7 includes an acoustic transformer 12, into which is integrated an acoustic transmitter 8 and an acoustic receiver 10. The acoustic transformer 12 is located with a transmission and reception control portion 19 and the evaluation unit 6 in a sensor housing 15. A flange ring 18 is attached to the outer jacket of the sensor housing 15. This flange ring 18 guides screws of screw joints 24, which are screwed into a mounting plate 29 on a container 2. Between the mounting plate 29 and the flange ring 18, there is provided a gasket 30. The terminal segment of the sensor housing 15 facing away from the container 2 is closed by a cover 26. Measurement lines 25 from the acoustic receiver 10 are conducted through the cover 26 and can be connected to a display unit 50 and/or a measurement storage device 60, etc., which are shown schematically.

In the container 2 reside two fluids 4 and 5, between which there lies a phase boundary surface 3 as indicated. The sensor 7 is preferably located above the phase boundary surface 3 in the fluid 4. At some distance in front of a provided acoustic transformer contact surface 13, which is mounted flush with an outer surface of a wall 14 of the sensor housing 15, there is positioned a reflector 9. The reflector 9 includes a reflector pole 20, which is screwed into a reflector plate 17. A head segment 28 of the reflector pole 20 is oriented toward the acoustic transformer contact surface 13 and is provided with rounded edges. Between the head segment 28 of the reflector pole 20 and the acoustic transformer contact surface 13, a measurement zone 11 is defined, which is penetrated by the sound waves. The measurement zone 11 thus has defined geometric dimensions, so that the fluids flowing through the measurement zone 11 in a creep flow can be detected. The distance of the head segment 28 of the reflector pole 20 from the acoustic transformer contact surface 13 can be several centimeters, for example. For the calibration of the reflector pole 20, the reflector pole 20 can be twisted in a threaded hole 22 provided in the reflector plate 17. The reflector plate 17 is mounted on spacers 16, so that the reflector level is oriented parallel to the plane of the acoustic transformer contact surface 13. The fastening of the reflector plate 17 to the spacers 16 and the spacers 16 to the sensor housing 15 is carried out by means of screw connections 23. The number of spacers 16 to be used can be varied as a function of the diameter of the sensor housing 15. Preferably, four spacers 16 are used, since such an arrangement avoids any adverse effect on the creep flow in the vicinity of the measurement zone 11. The installation of the measurement apparatus 1 is preferably done such that the measurement zone 11 is oriented horizontally, as shown.

The size of the acoustic transformer contact surface 13 is preferably several square centimeters. To avoid or eliminate extreme contamination of the acoustic transformer contact surface 13, there can preferably be a cleaning device provided. This cleaning device can preferably be provided with a strip-shaped wiper element 27, as illustrated in FIG. 1, and can be pivoted back and forth in contact with the acoustic transformer contact surface 13 by means of a motorized drive 70. The motorized drive 70 can be located in or on the sensor housing 15. When the wiper element 27 is activated, any smears or pits which are formed on the acoustic transformer contact surface do not adversely effect the measurement process, since no optical measurements need to be detected.

For the measurement apparatus 1 described above, the sound waves emitted by the acoustic transformer 12 are reflected by the reflector pole 20 and detected by the receiver portion of the acoustic transformer 12. By means of an electrical comparison of the transmitted signals and the reflected signals with regard to intensity and/or phase and delay, a measurement is obtained which describes the acoustic propagation impedance of the fluid in the measurement zone 11. Thus, a boundary layer detection for any kind of oil-water emulsion and free seawater is possible. If, during the measurement, the phase boundary surface 3 between the fluids 4 and 5 rises or sinks on account of process factors (or die to various physical displacements or disturbances), the fluid in the measurement zone 11 is replaced. On account of the large exposed diameter of the measurement zone 11, free-flowing fluids up to viscosities of about 10000 centi-Stokes can be measured. On account of the optimized configuration of the measurement zone 11, the acoustic transformer contact surface 13, and of the reflector pole 20, the disruptive influence of adhering fluid components is reduced to a minimum. Their layer thickness remains limited to a few millimeters, so that any interference is within a range which still permits precision measurement. By means of a suitable configuration of the evaluation unit 6, in connection with the transmission and receiving control portion 19, the measurement evaluation before the signal output can be done in less than one second.

Preferably, signal processing circuitry 70 is provided for receiving electrical signals form the acoustic receiver 10 and for processing these electrical signals to display the relative depth of the boundary layer 3 on a display device 50, or to store the results of the signal processing in a storage device 60, preferably an electonic storage device (e.g., RAM). Signal processing circuitry 70 which may be employed is well known to those of ordinary skill in the art of sonar and is disclosed, for example, in U.S. Pat. No. 4,323,992 entitled "Depth Sounder Repeater Structure and Method" and issued on Apr. 6, 1982; U.S. Pat. No. 4,939,699 entitled "Sonar System" and issued on Jul. 3, 1990; U.S. Pat. No. 4,420,824 entitled "Sonar Apparatus Having Improved Gain Control" and issued on Dec. 13, 1983; and U.S. Pat. No. 4,928,525 entitled "Sonic Tank Inventory Control System and Method."

By means of a temperature measurement element 80, temperature effects on the measurement. This temperature measurement element 80 is preferably located in the wall 14 of the sensor housing 15 and is connected to the evaluation unit 6. The acoustic transformer 12 can also be designed differently. For example, electrodynamic, magnetostrictive and piezo-ceramic devices can be used, whereby selection among such devices is a function of the desired frequency range. Basically, acoustic transmission frequencies from the ultrasound range up to the megahertz range are possible. The selection of the frequency is a function of the required resolution. The higher the desired resolution, the higher the acoustic frequencies must be. The selection of the transmission frequency is also a function of the physical characteristics of the fluids to be detected and of the transmission process used. In the ultrasound range, both a continuous transmission with detection of the phase shift and damping can be done, as can a burst (e.g., a sine beat) pulse process with a measurement of the propagation time (or echo time) and damping. In the megahertz range, on the other hand, a burst pulse process is preferably employed, with a measurement of the propagation time and the damping. The transmission frequency can also be generated by a freely-vibrating oscillator, whereby the propagation time (or echo time) of the acoustic signal through the fluid is measured, and the frequency is determined therefrom as a characteristic material property for the fluid in question.

One feature of the invention resides broadly in a process for the detection of phase boundary surfaces or layers of different, non-mixable fluids which are separated by gravity separation, characterized by the fact that sound waves are sent into the fluid by an acoustic transmitter, and the sound waves are reflected by a reflector located at a fixed distance from the acoustic transmitter to an acoustic receiver, and by the fact that thereafter, by means of an electrical comparison of the transmitted signals and the reflected signals, the acoustic propagation impedance of the fluid located in the measurement zone between the acoustic transmitter and reflector is determined, and the phase boundary surface or layer is determined therefrom.

Another feature of the invention resides broadly in a process characterized by the fact that the acoustic transmitter is operated at a continuous transmission frequency between 15 kHz and 50 kHz.

A yet another feature of the invention resides broadly in a process characterized by the fact that pulse packets with a base frequency between 15 kHz and 50 kHz are transmitted during a transmission phase, and then the reflected signal is received and the transmission of the next pulse packet is electronically triggered, whereby the frequency of the pulse packets transmitted (frequency) represents a yardstick for the characteristic material property being evaluated.

A still another feature of the invention resides broadly in a process for the detection of phase boundary surfaces or layers of different fluids which are not mixable and are separated by gravity separation, characterized by the fact that pulse-like sound waves are transmitted through the fluid by an acoustic transmitter at a frequency in the megahertz range, and are reflected by a reflector located at a fixed distance from the acoustic transmitter to an acoustic receiver, and by the fact that the propagation time (echo time?) and the intensity attenuation of the packets of sound waves reflected to the acoustic receiver are measured, and the phase boundary surface or layer is determined from these measurements.

A yet still another feature of the invention resides broadly in a process characterized by the fact that the transmission frequency is a maximum of six megahertz.

A still yet another feature of the invention resides broadly in a measurement apparatus with an electronic evaluation unit for the performance of the process characterized by the fact that the evaluation unit 6 is connected to a sensor 7 through which the fluid to be detected circulates, which sensor has an acoustic transmitter 8, a reflector 9 and an acoustic receiver 10, whereby the reflector 9 is located at some distance from the acoustic transmitter 8 and acoustic receiver 10, forming a geometrically defined measurement zone 11 filled with the fluid 4 to be detected 4 between the reflector 9 and acoustic transmitter 8 and acoustic receiver 10.

A further feature of the invention resides broadly in a measurement apparatus characterized by the fact that the acoustic transmitter 8 and the acoustic receiver 10 are designed as a one-piece acoustic transformer 12, whose acoustic transformer contact surface 13 corresponding to the reflector 9 is located in the one wall 14 of a pressure-tight sensor housing 15, in front of which the reflector 9 is held at a distance by means of spacers 16.

A yet further feature of the invention resides broadly in a measurement apparatus characterized by the fact that the reflector 9 is located on a reflector plate 17, which is connected to the spacers 16.

A still yet further feature of the invention resides broadly in a measurement apparatus characterized by the fact that a flange ring 18 is attached to the sensor housing 15, sealing the latter against the fluid 4, 5, and the sensor housing 15 is fastened by means of this flange ring 18 to the container 2 holding the fluid 4, 5.

A yet still further feature of the invention resides broadly in a measurement apparatus characterized by the fact that the acoustic transformer contact surface 13 is connected flush with the outer surface of the wall 14 of the sensor housing 15 facing the fluid 4, 5.

A still further feature of the invention resides broadly in a measurement apparatus characterized by the fact that the acoustic transformer 12 and the evaluation unit 6 are designed to be explosion-proof (or flame-proof) for Zone 0 hazardous locations.

A further feature of the invention resides broadly in a measurement apparatus characterized by the fact that the acoustic transformer 12 and the evaluation unit 6 are located in a sensor housing 15 which is explosion-proof (or flame-proof?) for Zone 0 hazardous locations.

A still another feature of the invention resides broadly in a measurement apparatus characterized by the fact that the acoustic transformer 12 is located with the transmitter and receiver control portion 19 and the evaluation unit 6 in the sensor housing 15.

A yet still further feature of the invention resides broadly in a measurement apparatus characterized by the fact that the acoustic transformer 12 and the amplifier stage connected to it, if any, are located in the sensor housing 15, and the transmitter and receiver control portion 19 and the evaluation unit 6 are located in a separate housing or in an equipment rack.

A still another feature of the invention resides broadly in a measurement apparatus characterized by the fact that a cleaning device for the acoustic transformer contact surface 13 is located on the wall 14 of the sensor housing 15 facing the fluid 4, 5.

A yet another feature of the invention resides broadly in a measurement apparatus characterized by the fact that the cleaning device has a strip-shaped wiper element 27 which can be moved back and forth in contact over the acoustic transformer contact surface 13 by means of a motorized drive.

A still another feature of the invention resides broadly in a measurement apparatus characterized by the fact that the reflector 9 is designed as a reflector pole 20.

A still yet another feature of the invention resides broadly in a measurement apparatus characterized by the fact that the reflector pole 20 of the acoustic transformer contact surface 13 is located facing the reflector plate 17, projecting from its plane.

A still yet another feature of the invention resides broadly in a measurement characterized by the fact that the head segment of the reflector pole 20 has rounded edges.

A still further feature of the invention resides broadly in a measurement apparatus characterized by the fact that the distance of the reflector pole 20 from the acoustic transformer contact surface 13 can be adjusted.

Another feature of the invention resides broadly in a measurement apparatus characterized by the fact that the reflector pole 20 is held in a threaded hole 22 of the reflector plate 17 by means of an external thread 21.

A yet another feature of the invention resides broadly in a measurement apparatus characterized by the fact that, in the vicinity of the wall 14 of the sensor housing 15 facing the fluid 4, 5, there is a temperature measurement element, whose signal compensates for thermal effects on the measurement signal by means of a logic circuit inside the electronic evaluation unit 6.

All, or substantially all, of the components and methods of the various embodiments may be used with at least one embodiment or all of the embodiments, if any, described herein.

All of the patents, patent applications and publications recited herein, if any, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The invention as described hereinabove in the context of the preferred embodiments is not to be taken as limited to all of the provided details thereof, since modifications and variations thereof may be made without departing from the spirit and scope of the invention.

What is claimed is:

1. A process for the detection of a boundary surface between a first fluid and a second fluid, the boundary surface being located between a first layer of the first fluid and a second layer of the second fluid, said process comprising the steps of:

providing an acoustic source for generating transmitted sound waves when actuated;

positioning said acoustic source such that said transmitted sound waves propagate through at least one of the first and second layers of fluids during said actuation of said acoustic source;

providing reflector means for being impinged upon by said transmitted sound waves and for reflecting said impinging transmitted sound waves to produce reflected sound waves;

said reflector means being positioned a distance from said acoustic source and defining a zone of measurement therebetween;

providing receiver means for receiving said reflected sound waves and for registering the reception of said reflected sound waves;

actuating said acoustic source to thereby generate said transmitted sound waves;

registering the reception of said reflected sound waves with said receiver means;

comparing said transmitted sound waves generated by said acoustic source to said reflected sound waves received by said receiver means;

employing the results of said comparison to determine at least the acoustic propagation impedance within said zone of measurement;

using at least said determined acoustic propagation impedance to determine the position of the boundary layer between the first and second layers of fluids.

2. A process according to claim 1, wherein, during said step of actuating said acoustic source to thereby generate said sound waves, said generated sound waves comprise substantially continuous sound waves which include a frequency component between about 15 KHz and about 50 KHz.

3. The process according to claim 1, wherein said step of actuating said acoustic source to thereby generate said transmitted sound waves and said step of registering the reception of said reflected sound waves with said receiver means are performed in alternating succession, wherein said reception of said reflected sound waves by said receiver means actuates said acoustic source to thereby cause the generation of said transmitted sound waves, and wherein the frequency of said transmitted sound waves are employed to determine a characteristic material property of at least one of said first and second fluids.

4. The process according to claim 2, wherein said step of actuating said acoustic source to thereby generate said transmitted sound waves and said step of registering the reception of said reflected sound waves with said receiver means are performed in alternating succession, wherein said reception of said reflected sound waves by said receiver means actuates said acoustic source to thereby cause the generation of said transmitted sound waves, and wherein the frequency of said transmitted sound waves are employed to determine a characteristic material property of at least one of said first and second fluids.

5. The process according to claim 1, wherein said transmitted sound waves are in the megahertz range, wherein said distance between said acoustic source and said reflector means is fixed, and wherein said comparison of said transmitted sound waves with said reflected and received sound waves comprises the steps of:
   a) determining the propagation time of said transmitted sound waves from said acoustic source to said reflector means and, thereafter, to said receiver means; and
   b) determining an intensity difference between said transmitted sound waves and said reflected and received sound waves.

6. The process according to claim 2, wherein said transmitted sound waves are in the megahertz range, wherein said distance between said acoustic source and said reflector means is fixed, and wherein said comparison of said transmitted sound waves with said reflected and received sound waves comprises the steps of:
   a) determining the propagation time of said transmitted sound waves from said acoustic source to said reflector means and, thereafter, to said receiver means; and
   b) determining an intensity difference between said transmitted sound waves and said reflected and received sound waves.

7. The process according to claim 3, wherein said transmitted sound waves are in the megahertz range, wherein said distance between said acoustic source and said reflector means is fixed, and wherein said comparison of said transmitted sound waves with said reflected and received sound waves comprises the steps of:
   a) determining the propagation time of said transmitted sound waves from said acoustic source to said reflector means and, thereafter, to said receiver means; and
   b) determining an intensity difference between said transmitted sound waves and said reflected and received sound waves.

8. The process according to claim 5, wherein said transmitted sound waves have a maximum frequency of substantially about 6 megahertz.

9. A measurement apparatus for detecting a boundary surface between a first layer of a first fluid and a second layer of a second fluid, said measurement apparatus comprising:
   sensor means for transmitting, reflecting and receiving sound waves, and for producing electrical signals in response thereto; and
   signal processing circuitry for receiving said electrical signals from said sensor means and for processing said electrical signals to thereby detect said boundary surface;
   said sensor means comprising:
   acoustic transmission means for transmitting sound waves into at least one of said first layer of fluid and said second layer of fluid; and
   reflector means for reflecting said transmitted sound waves;
   said reflector means being positioned a distance from said acoustic transmission means and defining a zone of measurement therebetween;
   said zone of measurement including at least a portion of at least one of said first layer of fluid and said second layer of fluid;
   wherein said sensor means additionally comprises;
   an integrally formed acoustic transformer;
   said integrally formed acoustic transformer being substantially contained within a substantially pressure tight housing; and
   an acoustic transformer contact surface provided on a peripheral exterior surface of said substantially pressure tight housing;
   wherein said reflector means comprising a reflector member; and
   wherein said measurement apparatus additionally comprises at least one spacer member for positioning said reflector member at said distance from said acoustic transformer contact surface.

10. The measurement apparatus according to claim 9, said sensor means further comprising a reflector mounting member connected to said at least one spacer member, said reflector member being mounted on said reflector mounting member.

11. The measurement apparatus according to claim 9, wherein said boundary surface is positioned within a vessel, and wherein said sensor means additionally comprises a flange member extending from said substantially pressure tight housing and connection means for connecting said flange member to the vessel.

12. The measurement apparatus according to claim 9, wherein said acoustic transformer contact surface is aligned substantially flush with said peripheral exterior surface of said substantially pressure tight housing.

13. The measurement apparatus according to claim 9, wherein said sensor means and said signal processing circuitry are designed to be at least one of explosion proof and flame proof for Zone 0 hazardous locations.

14. The measurement apparatus according to claim 9, wherein said signal processing circuitry and said acoustic transformer are located within said substantially pressure tight housing, and wherein said substantially pressure tight housing is designed to be at least one of explosion proof and flame proof for Zone 0 hazardous locations.

15. The measurement apparatus according to claim 9, wherein said sensor means further comprises amplifier means for amplifying said electrical signals, said amplifier means being located within said substantially pressure tight housing, and wherein said signal processing circuitry is located exterior of said substantially pressure tight housing in at least one of a separate housing and an equipment rack.

16. The measurement apparatus according to claim 9, said measurement apparatus additionally comprising cleaning means for cleaning said acoustic transformer contact surface, said cleaning means comprising a strip-shaped wiper member and motorized drive means for providing reciprocating and contacting movement of said strip-shaped wiper member over said acoustic transformer contact surface.

17. The measurement apparatus according to claim 10, wherein said reflector member comprises a reflector pole, said reflector pole being provided with a head portion, said head portion of said reflector pole having rounded edges, wherein said reflector pole faces and projects from a surface of said reflector mounting member, and wherein said measurement apparatus additionally comprises means for adjusting the distance between said reflector pole and said acoustic transformer contact surface.

18. The measurement apparatus according to claim 17, wherein said means for adjusting comprises a threaded hole formed in said reflector mounting member and an external thread formed on said reflector member.

19. The measurement apparatus according to claim 9, said measurement apparatus further comprising temperature sensing means for sensing the temperature of at least one of said first fluid and said second fluid, said temperature sensing means being positioned on the peripheral of said substantially pressure tight housing, and wherein said signal processing circuitry additionally comprises means for receiving a signal from said temperature sensing means and for compensating for thermal effects based upon said signal received from said temperature sensing means.

* * * * *